United States Patent [19]

Matsumura

[11] Patent Number: 5,018,851
[45] Date of Patent: May 28, 1991

[54] SLIT ILLUMINATING APPARATUS
[75] Inventor: Isao Matsumura, Yokosuka, Japan
[73] Assignee: Canon Kabushiki Kaisha, Tokyo, Japan
[21] Appl. No.: 430,896
[22] Filed: Oct. 31, 1989

Related U.S. Application Data
[63] Continuation of Ser. No. 158,657, Feb. 22, 1988, abandoned.

[30] Foreign Application Priority Data
Feb. 28, 1987 [JP] Japan .................. 62-46349
[51] Int. Cl.⁵ .................................. A61B 3/10
[52] U.S. Cl. .................................. 351/214; 351/213; 351/219; 351/221

[58] Field of Search ............ 351/205, 212, 214, 213, 351/221, 219

[56] References Cited
U.S. PATENT DOCUMENTS
4,293,198 10/1981 Kohayakawa et al. ............ 351/214

Primary Examiner—Paul M. Dzierzynski
Attorney, Agent, or Firm—Fitzpatrick, Cella, Harper & Scinto

[57] ABSTRACT

A slit illuminating apparatus in which slit illuminating light beams can be simply applied to an eye to be examined from different directions of application at a time or with lapse of time.

15 Claims, 2 Drawing Sheets

SLIT ILLUMINATING APPARATUS

BACKGROUND OF THE INVENTION

1. Field of the Invention

This invention relates to a slit illuminating apparatus used for ophthalmic clinical examination or the like.

2. Related Background Art

A slit lamp is an apparatus for applying a slit-like light beam to a conjunctiva, a cornea, a chamber angle, a crystalline lens, a vitreous body, an eye fundus or the like to observe an eye to be examined directly by means of a finder or indirectly through a monitor. In the slit illuminating apparatus according to the prior art, a slit-like light beam is projected from one direction and therefore, depending on the direction of observation, it is difficult to see the eye to be examined and it is necessary to rotate the entire slit illuminating optical system about the eye to be examined each time, and this is cumbersome. Further, with this prior art apparatus, it is impossible to set two directions at time and turn on the apparatus alternately to analyze the shape of the eye to be examined from the difference in contrast or to illuminate the eye to be examined from two directions at a time to confirm the whole aspect, and further to reproduce the two directions when illuminating.

As shown in Japanese Laid-Open Patent Application No. 34529/1987, there is known a slit projection apparatus for projecting a slit image onto an eye to be examined at a variable angle of elevation, but in such apparatus, a mirror and a lens are varied or a polarizing prism for forming a particular direction of application is used and it is impossible to irradiate the eye to be examined simply from any different direction of application.

SUMMARY OF THE INVENTION

It is an object of the present invention to provide a slit illuminating apparatus which is capable of simply illuminating a body to be examined from a plurality of directions at a time or with lapse of time.

It is also an object of the present invention to provide a slit illuminating apparatus in which the entire illuminating system need not be moved and the number of movable portions is small.

It is another object of the present invention to provide a slit illuminating apparatus which can apply a slit light beam from any direction without varying an imaging optical system for projecting a slit light beam onto a body to be examined.

DESCRIPTION OF THE PREFERRED EMBODIMENTS

Figure 1:
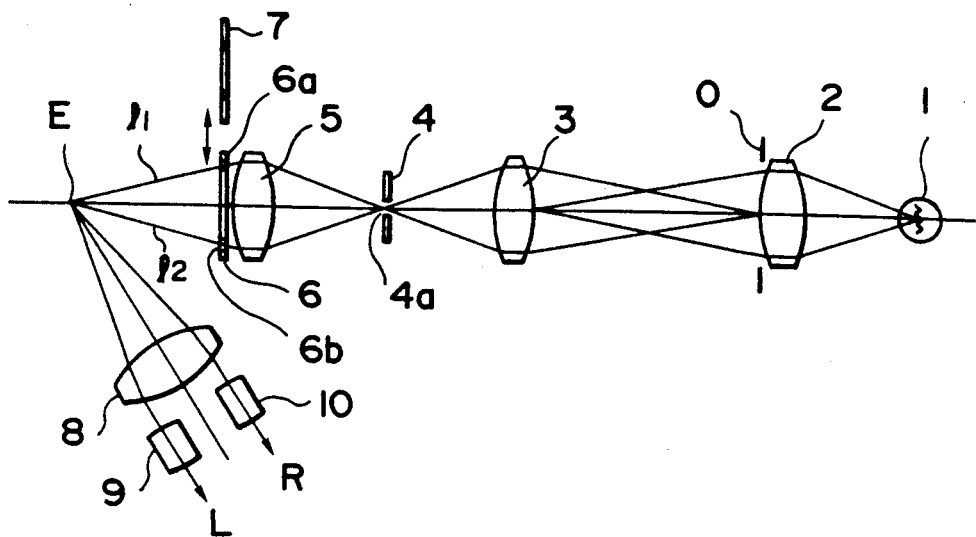
FIG. 1 shows the construction of a first embodiment of the present invention.
Figure 2:
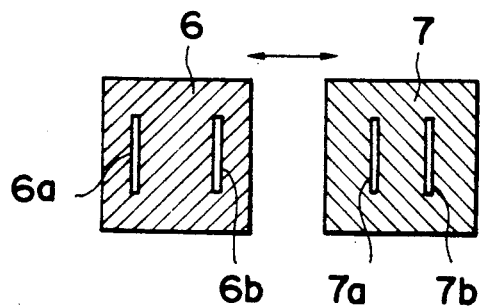
FIG. 2 is a plan view of a light beam regulating stop plate.

Referring to FIG. 1 which shows the construction of the present invention, the reference numeral 1 designates a light source, and on the optical path of the light source 1, there are successively disposed a condenser lens 2, a relay lens 3, a slit plate 4 having a slit 4a, an objective lens 5 and a light beam regulating stop plate 6 having stops 6a and 6b which are light beam passing areas, toward an eye E to be examined. The light beam regulating stop plate 6 is adapted to be inserted in the optical path alternately with a light beam regulating stop plate having stops 7a and 7b disposed at a different interval from the stops 6a and 6b, as shown in FIG. 2. Further, sideways of an illuminating system with respect to the position of the eye E to be examined and obliquely forwardly of the eye to be examined, there are disposed an objective lens 8 and magnification changing lens systems 9 and 10 for stereoscopic observation.

A light beam emitted from the light source 1 passes through the condenser lens 2 and the relay lens 3 and illuminates the slit 4a in the slit 4. At this time, this optical system constitutes a so-called Keiler illuminating optical system in which the image of the light source 1 is formed on the pupil of the relay lens 3 by the condenser lens 2 and the pupil 0 of the condenser lens 2 is formed on the slit plate 4 by the relay lens 3. The light beam passed through the slit 4a is imaged on the eye E to be examined through the objective lens 5 and the light beam regulating stop plate 6. On the other hand, the slit-illuminated eye E to be examined is stereoscopically observed by means of an observation optical system having two optical paths L and R constituted by the objective lens 8, the magnification changing lens systems 9 and 10, etc. The magnification changing lens systems 9 and 10 are optical systems for left and right eyes for stereoscopically observing, and the examiner may stereoscopically observe the slit-illuminated eye E to be examined through the magnification changing lens systems 9, 10 and further through finder optical systems for left and right eyes, not shown.

The light beam regulating stop plates 6 and 7 are members for regulating the direction of application of the slit light beam which illuminates the eye E to be examined. The light beam regulating stop plates 6 and 7, as shown in FIG. 2, are provided with light beam stops 6a, 6b and 7a, 7b, respectively, which are disposed at different intervals, and two slit light beams $l_1$ and $l_2$ for illuminating the eye E to be examined are obtained from these light beam stops 6a, 6b or 7a, 7b.

Figure 3:
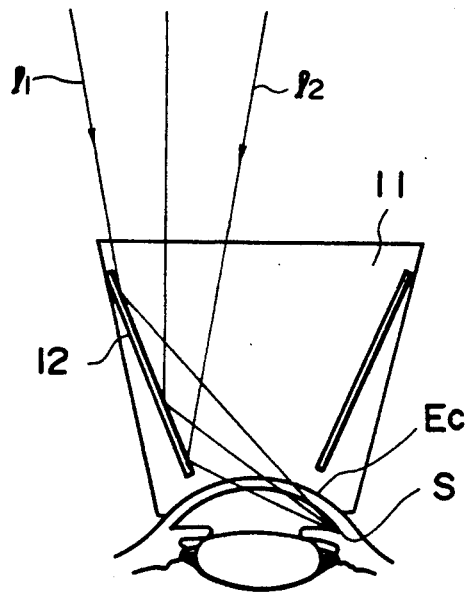
FIG. 3 shows the positional relation between slit light beams and an eye to be examined.

When for example, the chamber angle of the eye E to be examined is to be observed by the use of this ophthalmic slit illuminating apparatus, as shown in FIG. 3, the slit light beams $l_1$ and $l_2$ are caused to enter a chamber angle lens 11 mounted on the cornea Ec of the eye E to be examined, are reflected by a mirror 12, and irradiate the chamber angle S through the cornea Ec and the anterior. Thereupon, the chamber angle S is illuminated by a slit light beam toward the cornea Ec provided by the slit light beam 1 and a slit light beam toward the iris provided by the slit light beam $l_2$.

Figure 4:
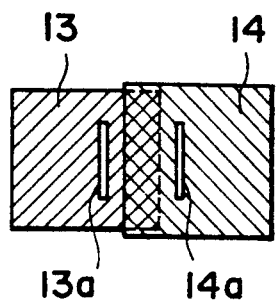
FIGS. 4, 5 and 7 are plan views of other light beam regulating stop plates.

Also, if in this case, the light beam regulating stop plates 6 and 7 are replaced with a light beam regulating stop plate 13 having a light beam stop 13a and a light beam regulating stop plate 14 having a light beam stop 14a which are shown in FIG. 4 and the light beam regulating stop plates 13 and 14 are inserted into the optical path at a time, the interval between the light beam stops 13a and 14a can be varied by changing the area of the portion in which the stop plates 13 and 14 overlap each other, and it becomes possible to apply the two slit light beams $l_1$ and $l_2$ to the eye E to be examined at any angle.

Figure 5:
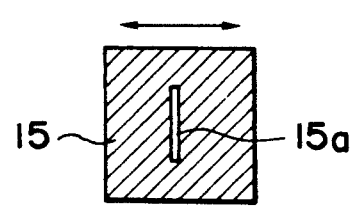

Further, if a light beam regulating stop plate 15 having a light beam stop 15a as shown in FIG. 5 is scanned with time by the use of the stop plate 15 instead of the light beam regulating stop plate 6, the angles of incidence of the slit light beams onto the eye E to be examined can be continuously varied.

Figure 6:
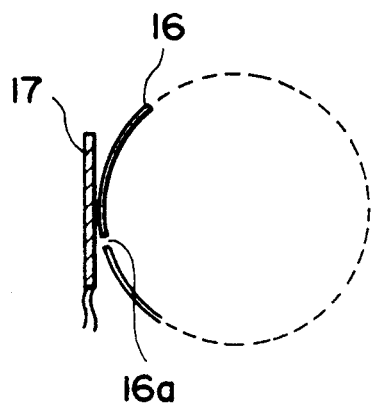
FIG. 6 illustrates still another light beam regulating stop plate.

FIG. 6 shows a case where a cylindrical light beam regulating stop plate 16 having a light beam stop 16a is provided at the location of the light beam regulating stop plate 6 of FIG. 1 and a liquid crystal shutter 17 is provided on that side of the stop plate 16 which is adjacent to the eye E to be examined. If the liquid crystal shutter 17 is opened and the light beam regulating stop plate 16 is rotated, the angles of incidence of the slit light beams onto the eye E to be examined can be continuously varied as in the case of FIG. 5. Also, if the liquid crystal shutter 17 is opened and closed while being controlled with time, the slit light beams enter the eye E to be examined only when the angles of incidence are predetermined ones. Further, if the opening-closing time of the liquid crystal shutter 17 is controlled a plurality of times within the width of the slit light beam passing through the objective lens 5, that is, the liquid crystal shutter 17 is opened and closed in synchronism with the speed of the rotating light beam regulating stop plate 16, slit light beams can be applied to the eye E to be examined from a plurality of directions substantially at a time.

Figure 7:
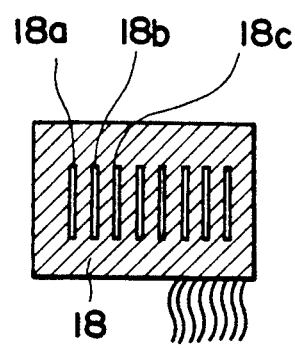

FIG. 7 shows another light beam regulating stop plate 18 having a plurality of light beam stops 18a, 18b, 18c, ... Liquid crystal shutter plates which can be individually opened and closed are combined with the respective light beam stops. The light beam regulating stop plate 18 is disposed at the location of the light beam regulating stop plate 6 of FIG. 1. By the plurality of light beam stops 18a, 18b, 18c, ... being suitably opened and closed by the liquid crystal shutter plates, a slit light beam can be applied to the eye E to be examined from any angle, and further, any number of slit light beams can be projected onto the eye E to be examined at a time.

Figure 8:
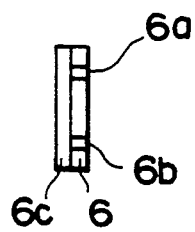
FIG. 8 shows a modification of the light beam regulating stop plate which is provided with a filter.

While in the above-described embodiment, description has been made only of the variation in the angles of incidence of the slit light beams, the illumination by a slit light beam of a wavelength corresponding to the angle of incidence becomes possible by increasing or decreasing the quantity of light of the slit light beam for the angle of incidence of each slit light beam or by providing a filter. This can be accomplished as by attaching a filter 6C such as an ND filter or a wavelength selecting filter to the light beam regulating stop plate 6 as shown in FIG. 8. Further, in the above-described embodiment, the illuminating optical system for illuminating the eye E to be examined has been described as being fixed, but of course, it may be designed so as to be rotatively displaceable about the eye E to be examined relative to the observation optical system.

Figure 9:
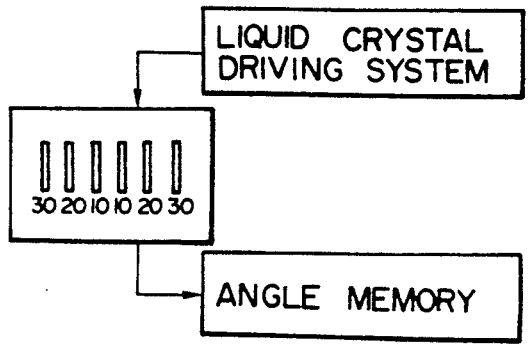
FIG. 9 shows a modification of the light beam regulating stop plate which is provided with an angle memory.

Also, the angles of incidence of the slit light beams onto the eye E to be examined need be memorized and displayed when the eye to be examined is to be diagnosed with reproducibility or for the purpose of setting particular angles of incidence during diagnosis, and it becomes possible to recognize the angles, for example, by attaching an angle scale or an angle indication to the light beam regulating stop plate as shown in FIG. 9, and further providing a memory for memorizing the angle of the light beam stop. Further, in the above-described embodiment, the direction of the slit plate 4 has been made constant, but alternatively, the slit plate 4 itself may be rotated about the optic axis in a plane perpendicular to the optic axis and in response thereto, the direction of the aperture stop in the light beam regulating stop plate may also be rotated so that for example, the lengthwise direction of the slit 4a may coincide with the lengthwise direction of the stops 6a and 6b of the light beam regulating stop plate 6.

I claim:

1. A slit lamp comprising:
    an illuminating optical system comprising imaging means for imaging a slit-like light beam on a portion of an eye to be examined; and
    an observation optical system for observing therethrough the portion of the eye to be examined illuminated by the slit-like light beam;
    said illuminating optical system including aperture means for regulating the direction of application of the slit-like light imaged by said imaging means so as to direct slit-like light beams in different directions at different times on the same portion of the eye to be examined, said aperture means being movable in a direction substantially crossing an optic axis of said imaging means.

2. A slit lamp according to claim 11, wherein said aperture means is a single element.

3. A slit lamp according to claim 4, and further includes selecting means for selecting a position to which said aperture means is moved.

4. A slit lamp according to claim 3, wherein said aperture means includes first and second elements for directing the slit-like light beam in different directions to the portion of the eye to eye examined.

5. A slit lamp according to claim 3, wherein said selecting means includes moving means for moving said aperture means in a direction perpendicular to an optic axis.

6. A slit lamp according to claim 3, wherein said selecting means includes moving means for moving said aperture means in a curved path and for positioning said aperture means, when in use, at the intersection of a plane tangential to the curved path and perpendicular to an optic axis and the optic axis.

7. A slit lamp according to claim 6, wherein said aperture means is movable to two locations with the optic axis interposed therebetween.

8. A slit lamp according to claim 6, wherein said aperture means includes a plurality of light transmitting elements spaced at predetermined intervals to transmit the slit-like light beam in one direction to the portion of the eye to be examined and a plurality of light transmitting elements spaced at predetermined intervals to transmit the slit-like light beam in another direction to the portion of the eye to be examined.

9. A slit lamp according to claim 3, wherein said aperture means includes two different areas each with a single opening.

10. A slit lamp according to claim 1, wherein said aperture means is movable to opposed locations with the optic axis interposed therebetween.

11. A slit lamp according to claim 1, wherein said aperture means is formed from liquid crystal.

12. A slit lamp according to claim 1, wherein said illuminating optical system includes a mirror for observing a chamber angle of the eye to be examined.

13. A slit lamp according to claim 1, wherein said observation optical system includes observing means for permitting stereoscopic observation.

14. A slit lamp according to claim 1, and further includes varying means for varying the quantity of light forming the slit-like light beam.

15. A slit lamp according to claim 1, and further includes rotating means for rotatably displacing said illuminating optical system relative to said observation optical systems about the eye to be examined.

* * * * *

UNITED STATES PATENT AND TRADEMARK OFFICE
CERTIFICATE OF CORRECTION

PATENT NO. : 5,018,851
DATED : May 28, 1991
INVENTOR(S) : ISAO MATSUMURA

It is certified that error appears in the above-identified patent and that said Letters Patent is hereby corrected as shown below:

COLUMN 2:

Line 23, "slit 4." should read --slit plate 4.--.
    Line 61, "beam 1" should read --beam $1_1$--.

COLUMN 4:

Line 31, "claim 11," should read --Claim 1,--.
    Line 33, "claim 4, and" should read --Claim 1, which--.
    Line 39, "eye" (second occurrence) should read --be--.

COLUMN 5:

Line 7, "and" should read --which--.

COLUMN 6:

Line 3, "and" should read --which--.
    Line 6, "systems" should read --system--.

Signed and Sealed this

Fifteenth Day of December, 1992

*Attest:*

DOUGLAS B. COMER

*Attesting Officer*      Acting Commissioner of Patents and Trademarks